United States Patent [19]

Habermeyer et al.

[11] Patent Number: 5,399,152
[45] Date of Patent: Mar. 21, 1995

[54] APPARATUS FOR TREATING FRACTURES IN EXTREMITIES

[76] Inventors: Peter Habermeyer, Oberfoehringer Strasse 27, München 81, Germany, 8000; Stefan Lederer, Soxhletstrasse 6, München 40, Germany, 8000; Andreas Hassler, Feldstrasse 11, Graefelfing, Germany, 8032

[21] Appl. No.: 856,230
[22] PCT Filed: Sep. 13, 1991
[86] PCT No.: PCT/EP91/01744
§ 371 Date: Jul. 9, 1992
§ 102(e) Date: Jul. 9, 1992
[87] PCT Pub. No.: WO92/04880
PCT Pub. Date: Apr. 2, 1992

[30] Foreign Application Priority Data

Sep. 13, 1990 [DE] Germany .......... 40 29 120.0

[51] Int. Cl.[6] ............................................. A61E 5/00
[52] U.S. Cl. ........................................ 602/23; 602/13; 602/6; 602/27
[58] Field of Search .......... 602/23, 27, 2, 5, 6, 602/12-14, 16, 20; 128/399, 402, 379; 607/108, 111, 112

[56] References Cited

U.S. PATENT DOCUMENTS

| | | | |
|---|---|---|---|
| 3,164,152 | 1/1965 | Nicoll | 602/13 |
| 3,701,349 | 10/1972 | Larson | 602/13 X |
| 3,745,998 | 7/1973 | Rose | 602/6 |
| 3,762,405 | 10/1973 | DeGeorge | 602/13 X |
| 4,505,269 | 3/1985 | Davies et al. | 602/27 |
| 4,572,169 | 2/1986 | Mauldin et al. | 602/27 |
| 4,657,003 | 4/1987 | Wirtz | 602/13 X |
| 4,862,879 | 9/1989 | Coombs | 602/5 X |
| 4,934,355 | 6/1990 | Porcelli | 602/16 |
| 4,974,583 | 12/1990 | Freitas | 602/27 X |
| 5,022,390 | 6/1991 | Whiteside | 602/23 |
| 5,070,868 | 12/1991 | Hepburn et al. | 602/27 |
| 5,078,128 | 1/1992 | Grum et al. | 602/23 |
| 5,092,321 | 3/1992 | Spadeuas | 602/27 |
| 5,176,623 | 1/1993 | Stetman et al. | 602/27 |

FOREIGN PATENT DOCUMENTS

| | | | |
|---|---|---|---|
| 2550443 | 2/1985 | France | 602/23 |
| 2712675 | 9/1978 | Germany | 602/10 |

Primary Examiner—Richard J. Apley
Assistant Examiner—Linda M. Dvorak
Attorney, Agent, or Firm—Townsend and Townsend Khourie and Crew

[57] ABSTRACT

An apparatus for treating fractures in extremities and regions of extremities which is in particular provided for the treatment of extremity fractures in the region of the lower leg, thigh, lower arm and upper arm has at least two shell parts which can be clamped relative to one another which enclose the extremity to be surrounded. Deformable and evacuatable vacuum-tight cushions having at least one valve and in which there are located a plurality of filling bodies, which are movable relative to one another, in particular small grained filling bodies, are provided between the shell parts and the extremity.

23 Claims, 8 Drawing Sheets

APPARATUS FOR TREATING FRACTURES IN EXTREMITIES

BACKGROUND OF THE INVENTION

The invention relates to an apparatus for the surroundive fixation of extremities and regions of extremities, in particular for the treatment of fractures of extremities in the region of the lower leg, thigh, lower arm and upper arm.

For the treatment of fractures of extremities, plaster casts or their modern variants in the form of plastic casts are usually applied. The application of such casts however not only requires considerable aptitude and corresponding time and effort for the personnel but also frequently leads to edges of projections of the inner side of the plaster or plastic cast giving rise to pressure points which are extremely disturbing for the patient. After the setting of the respective fracture the patient is exposed to the follow-up winding on of the bandages and waiting until the plaster has set. Finally, it is as a rule necessary, with known plaster or plastic casts, to change this plaster or plastic cast when, during the course of treating the fracture, the swelling of the relevant limb goes down. This is also a complicated process which is again unpleasant for the patient.

SUMMARY OF THE INVENTION

The object of the invention is to develop an apparatus of the initially named kind in such a way that the indicated disadvantages of plaster and plastic casts can be avoided, so that treating fractures in extremities is possible which can be rapidly effected and does not lead to any form of pressure points, the fixation being effective practically without delay and capable of being simply released and immediately reapplied.

This object is satisfied in accordance with the invention in that at least two shell parts are provided which can be mutually clamped together and which surround the extremity to be surrounded, and in that deformable evacuatable cushions which are made vacuum-tight and provided with at least one valve and in which there are located a plurality of filling bodies which are movable relative to one another, in particular small grained filling bodies, are provided between the shell parts and the extremity.

Through the evacuation which can be carried out within a short time the cushions, which are applied closely and in a fitted manner to the section of the limb to be treated, become hard and of stable form in the shape provided during the application procedure. Thus a very firm sleeve which is modelled well to the respective extremity arises in conjunction with the hard shell parts and cannot generate any pressure points in the region of the skin, since during hardening of this structure no radially inwardly directed pressure arises and since no edges or projections can also be formed at the inner side.

The closure members which are provided at the longitudinal edge regions of the foot part and of the shaft part which can consist of strip-like closure parts, but which preferably consist of latching devices with latch elements which can be plugged into one another, in accordance with claim 3, serve in a very simple and rapid manner for the light contact pressure necessary prior to evacuation of the cushions against the surrounded body part. In this manner a sleeve of absolutely correct fitted shape can be generated and can first be determined via the closure member. After evacuation a sleeve is then present which is solidified in itself and stabilised in its shape.

BRIEF DESCRIPTION OF THE DRAWINGS

The invention will now be explained in more detail by way of an embodiment and with reference to the drawing in which are shown.

DESCRIPTION OF THE PREFERRED EMBODIMENT

Figure 1:
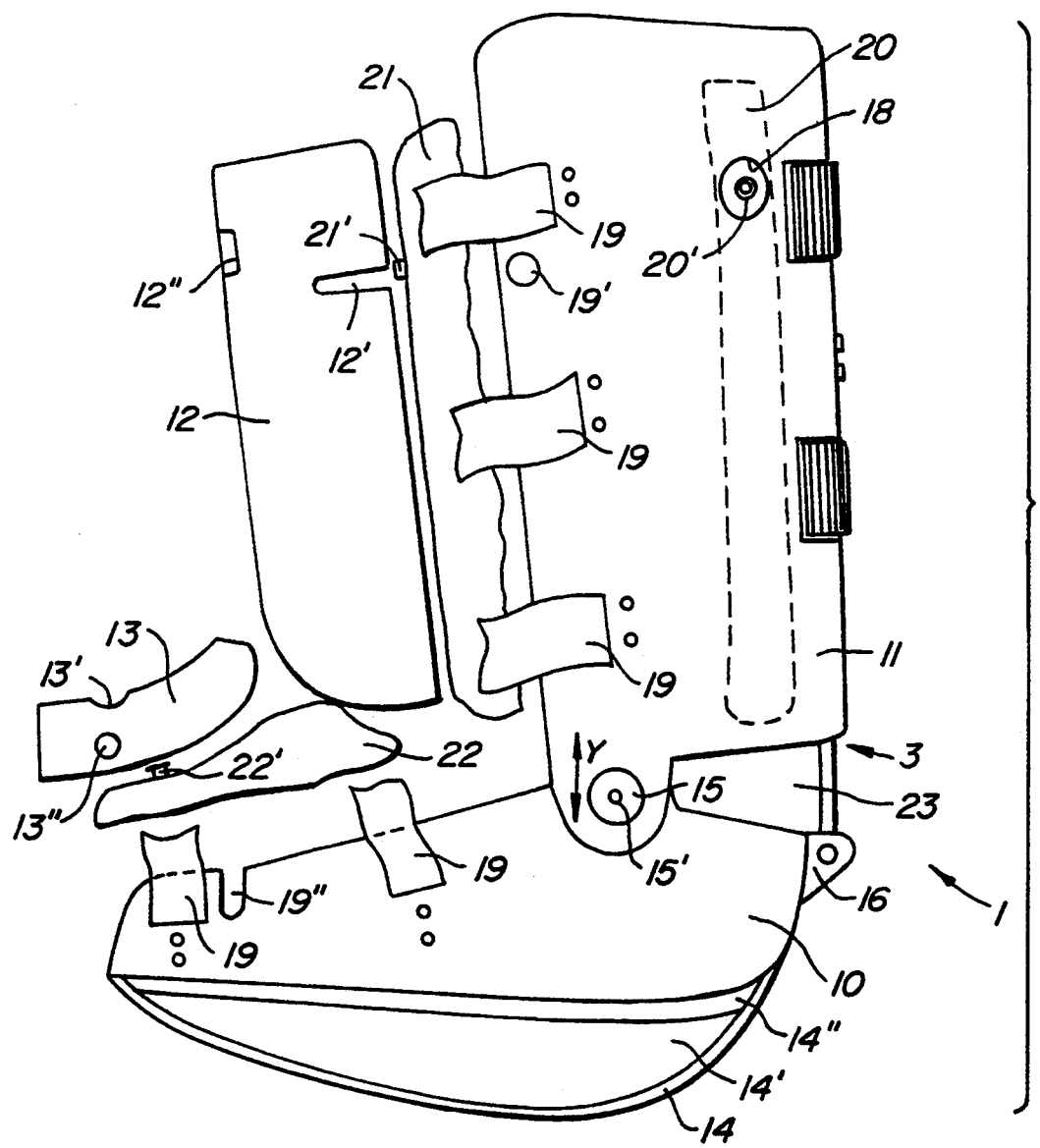
FIG. 1 a side view of an apparatus in accordance with the invention.

An apparatus for treating fractures in extremities is shown in FIG. 1 as a shell body 1 for the foot/lower limb region of a patient. The shell body 1 consist of a foot part 10 and also of a shaft part 11. The foot part 10 and the shaft part 11 are pivotally connected together via lateral hinges 15. The hinges preferably consists of plastic in order to permit the passage of X-radiation therethrough.

The foot part 10 is formed in shell-like manner so that it is upwardly open so that a receiving trough is provided for a foot. A walking sole 14 is provided at the lower side of the foot part 10 and the outer shape of the walking sole 14 is matched to the roll-off movement of the foot during walking. Between the sole 14 and the lower side of the shell of the foot part 10 there are provided damping layers 14', 14", and one of the layers can be a shock absorbing layer 14".

A bearing block 16 for an adjusting device 3 which will be explained later is mounted in the heel region of the foot part 10.

The shaft part 11 consists of an approximately half shell-like body with a housing section 17 being provided at its rear region for receiving the adjusting device 3. At least one opening 18 is provided in the rear side region, in the wall of the shaft part 11, and serves for the later explained passage of a valve 20'. The opening 18 preferably lies in the sidewall of the shaft part 11 which is directed towards the outer side of the body. A further opening 18 can however be optionally provided in the oppositely disposed sidewall of the shaft part 11 so that the apparatus can be used on both legs.

In the region of the front edges of the shaft part 11 at least one outwardly directed mushroom spigot 19' is arranged at each edge. The elasticity of the sidewalls of the shaft part 11 increases from the rear region of the shaft part 11 to its front edge 11'.

Several clamping elements are arranged along each front edge of the shaft part 11 and in each case two clamping elements 19 lying at the same level cooperate as a clamping device. The clamping elements 19 can for example be formed by a burr closure tape that is secured, for example riveted or adhesively bonded to the shaft part 11. Similar clamping device 19 are also provided at the free edges of the foot part 10. The foot part 10 has in each case at its upper edge in the front region a transverse slot 19'' which extends perpendicular to the edge. A shaft cover part 12 consists, in just the same way as the shell body 1 of a hard slightly resilient material, for example a plastic. The shaft cover shell 12 has in its upper region at the rear free edges of its sidewalls in each case a slot 12' into which the respective mushroom spigot 19' of the shaft part 11 is introduced so that in this way a guide is provided for the shaft cover shell 12 at the shaft part 11. At its front region the shaft cover shell 12 has in its wall an opening 12'' for the passage of a valve 21'.

A foot cover shell 13 is similarly formed to the shaft cover shell 12 and has at its upper side a wall opening 13' for the passage of a valve 22'. At its sides the foot cover shell 13 has in the region of its free edges, in each case, a mushroom spigot 13'' which together with the respective slot 19'' in the foot part 10 forms a guide for the foot cover shell 13.

Figure 2:
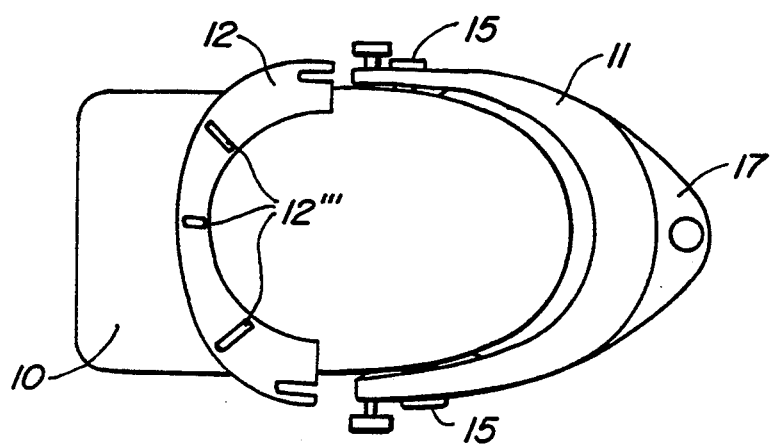
FIG. 2 a plan view on an apparatus in accordance with the invention.

The inner side of the shaft cover shell 12 and also the inner side of the foot cover shell 13 can be provided with ribs 12''', webs or other inwardly directed projections (FIG. 2). These projections hook together with the front cushion 21 and thus prevent the front cushion 21 sliding away. Similar formations can also be provided at the inner side of the foot cover shell 13 for the foot cushion 22 and/or at the inner side of the shaft part 11 for the rear cushion 20.

At the inner side of the shaft part a rear adaptive cushion 20 is provided either loosely contacting or secured to the shaft part—for example by a burr closure tape or adhesive. A front fitted cushion 21 is provided at the inner side of the shaft cover shell 12 and a like foot cushion 22 is provided at the inner side of the foot cover shell 13.

The rear cushion 20, the front cushion 21 and the foot cushion 22 consist of a vacuum tight bladder which is provided with at least one evacuation valve 20', 21', 22' and in the inner space of the bladder there is provided a plurality of filling bodies which are movable relative to one another. These filling bodies can for example be balls of Styropor (Registered Trade Mark) (polystyrene balls).

Figure 3:
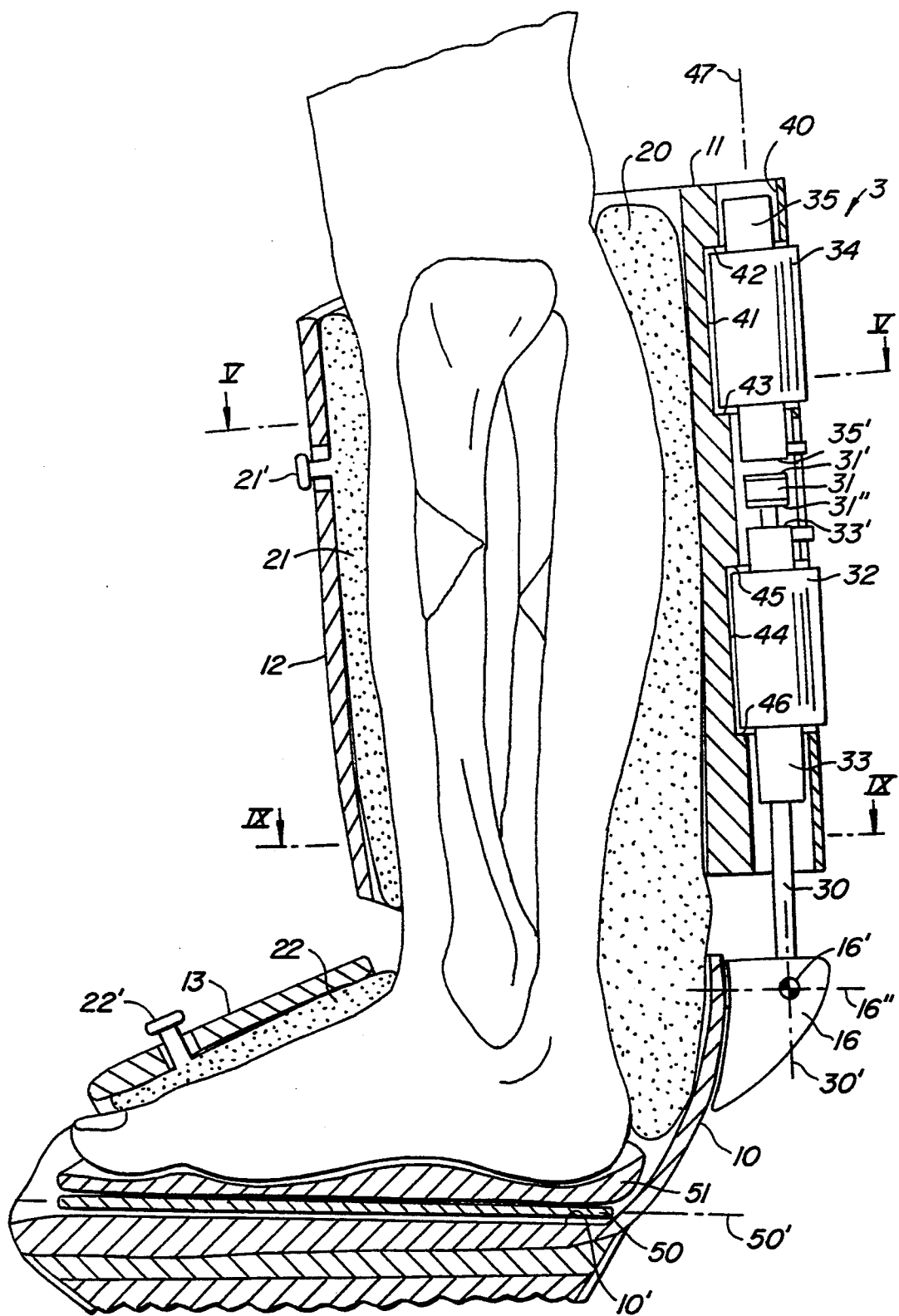
FIG. 3 a vertical section through the apparatus in accordance with the invention, FIG. 4 a section taken from FIG. 3, FIG. 5 a horizontal section through the apparatus in accordance with the invention along the line V in FIG. 3, FIG. 6 a horizontal section through a further apparatus in accordance with the invention similar to FIG. 5, FIG. 7 a partly sectioned side view of an apparatus in accordance with the invention with a removable running sole, FIG. 8 the plan view of an evacuatable cushion, FIG. 9 a horizontal section through a further apparatus in accordance with the invention at the level of the line IX—IX of FIG. 3.

In FIG. 3 the adjusting mechanism 3 can be seen for the adjustment of the angle of inclination between the foot part 10 and the shaft part 11 and also for the adjustment of the angular range in which the shaft part 11 can be pivoted relative to the foot part 10.

In the rear section of the shaft part 11 a channel 40 of round cross-section is provided in the longitudinal shaft direction. In the channel 40 there are formed two nut receiving locations 41, 44 which are spaced apart from one another. The diameter of the nut receiving locations is larger than that of the channel and the locations are open towards the rear side of the shaft part 11. The transitions between the channel 40 and the nut receiving sections 41, 44 form abutments 42, 43; 45, 46 which extend perpendicularly to the channel axis 47.

Tubular nuts which are provided at their outer periphery with knurling are inserted into the nut receiving locations 41, 44. The periphery of the nuts provided with the knurling is thereby accessible through the rear openings of the nut receiving locations 41, 44.

A threaded bar 35 is screwed into the upper adjusting nut 34 and the lower side of the threaded bar forms an abutment 35'. A threaded tube 33 is screwed into the lower adjusting nut 32 and has at its top side a ring, like abutment 33'. An anchor 30 which is for example formed by a metal bar is pushed through the threaded tube 33 and an abutment head 31 is fixedly attached to its upper end. The abutment head 31 is thereby disposed between the abutment 33' of the threaded tube 33 and the abutment 35' of the threaded bar 35. The upper end face of the abutment head 31 which points towards the abutment 35 forms an upper abutment 31' and the lower ring-like end face which points towards the abutment 33 forms a lower abutment 31''. The other end of the anchor 30 is hingedly journalled in the bearing block 16 at the foot part 10. The bearing axis 16' thereby lies at a right angle to the axis 30' of the anchor 30 and extends essentially parallel to the axis 15' of the two hinges between the shaft part 12 and the foot part 10.

Figure 4:
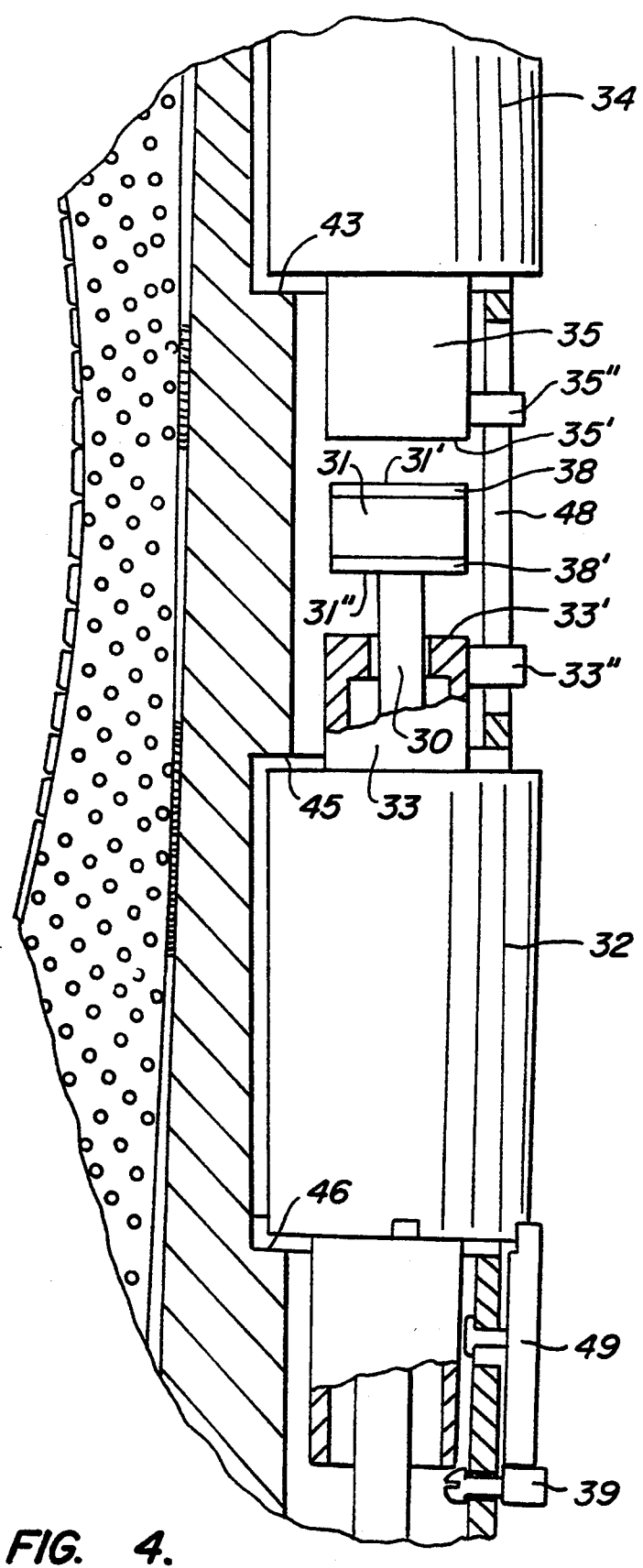

As can be seen from FIG. 4 the armature or anchor 30 is guided by the end wall of the threaded tube 33 in the region of the abutment 33' whereas over the remaining length of the threaded bar 33 its inner diameter is substantially larger than the diameter of the anchor 30. In this way a jamming of the anchor 30 in the threaded tube 33 is prevented during pivoting of the shaft part 11 about the foot part 10.

At the rear side of the shaft part 11 a slot 48 is provided between the nut receiving locations 41, 44 into which pins 33'', 35'' project from the inside. These pins are provided in the region of the respective abutments 33' or 35'' of the threaded tube 33 and of the threaded bar 35 and prevent them from rotating about their longitudinal axis within the channel 40.

By rotation of the upper adjusting nut 34 the threaded bar 35 is displaced along the channel 40. In the same manner the threaded tube 33 is displaced in the channel 40 by rotation of the lower adjusting nut 32. Thus, the position of the abutment 35' of the threaded bar 35 can be changed by rotation of the upper adjusting nut 34 and the position of the abutment 33' of the threaded bar 33 can be changed within the channel 40 by rotation of the lower adjustment nut 32. The abutment head 31 is essentially rigid with respect to the foot part in the direction of the channel axis 47 as a result of the firm connection with the foot part so that a pivotal movement of the shaft part 11 about the axis 15' is only permitted within the regions between the upper abutment 31' of the abutment head 31 and the abutment 35' of the threaded bar 35 and also between the lower abutment 31'' of the abutment head 31 and the abutment 33' of the threaded tube 33. In this arrangement the abutment 35' of the threaded bar 35 restricts the pivotal movement of the shaft part 11 to the rear whereas the abutment 33' of the threaded tube 33 restricts the pivotal range of the shaft part forwardly.

In this manner the permissible pivotal range of the shaft part 11 forwardly from a rest position which can be selected as desired can be set independently of the pivotal range from this rest position rearwardly. Moreover the shaft part 11 can be fixed in any angular position which is selectable between the adjustable angular positions, with both the threaded bar 35 and also the threaded tube 33 being brought into contact with the abutment head 31 and clamped. During this clamping the upper ring-like end face of the adjusting nut 34 is brought into contact with the upper abutment 42 of the upper nut receiving location 41 while the lower ring-like end face of the lower adjusting nut 32 enters into contact against the lower abutment 46 of the lower nut receiving location 44. As a result of this clamping the selected angular position of the shaft part 11 is fixed without play relative to the foot part 10.

In order to prevent unintentional rotation of the adjusting nuts 32 and 34 respectively it is possible to provide devices providing security against rotation of these nuts. For example a slider 49 associated with each of these nuts can be provided at the rear side of the shaft and can enter into form-locked engagement with the adjusting nuts 32 and 34 respectively in order to lock the same. The securing of the respective slider against unintentional release of this engagement can additionally take place for example through a plug 39 which is inserted into a bore accessible when the slider is blocked 49 in the rear side of the shaft part and is there prevented by latching from dropping out of place. If scales are applied to the outer side of the shaft part 11 along the slot 48 then the front and rear boundary angle can be read off through the pin 33" or 35" respectively which in this case additionally serves as a pointer. The upper abutment 31' and the lower abutment 32' of the abutment head 31 can be provided with a resilient and/or shock-absorbing layer 38, 38' so that blows during pivoting of the shaft part 11 relative to the foot part 10—for example during walking—can be damped and, if necessary, absorbed. A shock damping function can also be satisfied by a resilient mounting of the anchor 30 in the bearing block 16.

An intermediate sole 50 is arranged in the foot part 10 on the lower inner surface 10' of the trough of the foot part and can be inclined relative to the foot part 10 about an axis 50' which extends parallel to the longitudinal direction of the foot. Moreover, the distance of the intermediate sole 50 from the lower inner surface 10' of the foot part 10 can be varied. In this way the intermediate sole 50 can be adjusted both in its height and also in its inclination with respect to the inner surface 10' and can also be fixed in the selected position. The adjustment can take place by the insertion of elements between the inner surface 10' and the intermediate sole 50 or by a non-illustrated adjusting mechanism.

A foot bed 51 is arranged above the intermediate sole 50 and consists of a resilient shock damping material. A further adjustment possibility about an axis lying parallel to the longitudinal direction of the foot can be given in that the lateral hinges 15 are adjustable independently from one another in height (along the arrow Y in FIG. 1). If an adjustment of this kind is provided for the lateral inclination of the shaft part 11 relative to the foot part 10 then the bearing block 16 on the foot part 10 should likewise be pivotable about an axis 16" extending substantially parallel to the longitudinal direction of the foot in order to prevent strains within the adjusting mechanism 3'.

In the following the working and manner of operation of the apparatus will be described. The lower leg and foot of a patient are laid into the opened apparatus which is already provided with the rear cushion 20 and the foot bed 51 with the filling bodies having previously been distributed in the rear cushion 20 in such a way that the shape of the rear cushion 20 corresponds approximately to the shape of the rear lower limb and foot region of the patient.

Thereafter the lower limb and foot are aligned in the apparatus and, for example, for the alignment of a lower leg break, the elastic sidewalls of the shaft part 11 can be pressed to the side. Moreover the shape of the rear cushion 20 can be changed if required by displacement of the filling bodies. A free space 23 provided behind the hinges 15 in the region of the achilles tendon of the patient is advantageous for the access to the rear cushion 20.

Thereafter the front cushion 21 is laid onto the front lower leg region of the patient and the filling bodies are also displaced here in such a way that the cushion is adapted in the front region to the contour of the lower limb. Thereafter the shaft cover shell 12 is mounted onto the shaft part 11 outwardly overlapping (FIG. 5) the front edges of the shaft part 11, with the mushroom spigots 19' engaging into the slots 12'. The clamping devices at the front side of the shaft part 11 which, for example, consist of a burr closure tape are guided over the shaft cover shells and are tensioned there in such a way that they press the shaft cover shell against the lower limb lying in the apparatus. In the same manner the foot cushion 22 is laid onto the upper side of the foot of the patient and the foot cover shell 13 is placed in corresponding manner into the slots 19" of the foot part 10 and clamped with the clamping devices located there.

Finally the air is sucked out of the cushions 20, 21 and 22 through the valves 20', 21', 22' so that the filling bodies located in the respective cushion enter into close frictional contact and in this manner the respective cushion becomes essentially rigid in a shape matched to the lower limb or foot of the patient without however exerting a pressure on the patient.

After this step the clamping devices can be retensioned as required. The stiff and stable shells which are braced against the cushions which become hard through the evacuation ensure that the lower leg and the foot of the patient are then fixedly received in the apparatus.

As the application of the apparatus normally takes place while the patient is lying down a spacing can be present between the sole of the foot and the foot bed 51 which prevents uniform contact pressure of the foot. In this case the foot bed 51 can be moved up to the foot sole through a vertical adjustment of the intermediate sole 50 relative to the inner side of the foot part 10. The intermediate sole 50 can thereby be uniformly vertically adjusted over its entire length or also only regionally vertically adjusted.

For the ideal adaptation of the foot bed to the foot sole of the patient a canting adjustment can thereafter take place with the inclination of the intermediate sole 50 taking place about the axis 50'. For the case that an extremely pronounced canting correction is necessary, which can for example be the case with patients with pronounced bowlegs, the lateral inclination of the shaft part 11 relative to the foot part can also be changed by vertical adjustment of one or both hinges 15. In this manner both the foot and also the lower leg are firmly received in the apparatus but nevertheless without excessive pressure on the body of the patient.

A movement in the patient's ankle joint can be prevented in that the angle of inclination of the shaft part 11 relative to the foot part 10 about the axis 15' is fixedly adjusted by means of the two adjusting nuts 32 and 34. A selection of this fixedly adjusted angle can take place in dependence on the injury to be treated within the entire pivotal angular range which can be selected by the adjusting device.

With injuries which permit movement of the patient in the ankle joint region the pivotal angle about the axis 15' can be restricted by adjustment of the adjusting nuts 32 and 34, with it being possible to set the maximum pivotal movement forwardly and the maximum pivotal movement rearwardly independently of one another.

Figure 6:
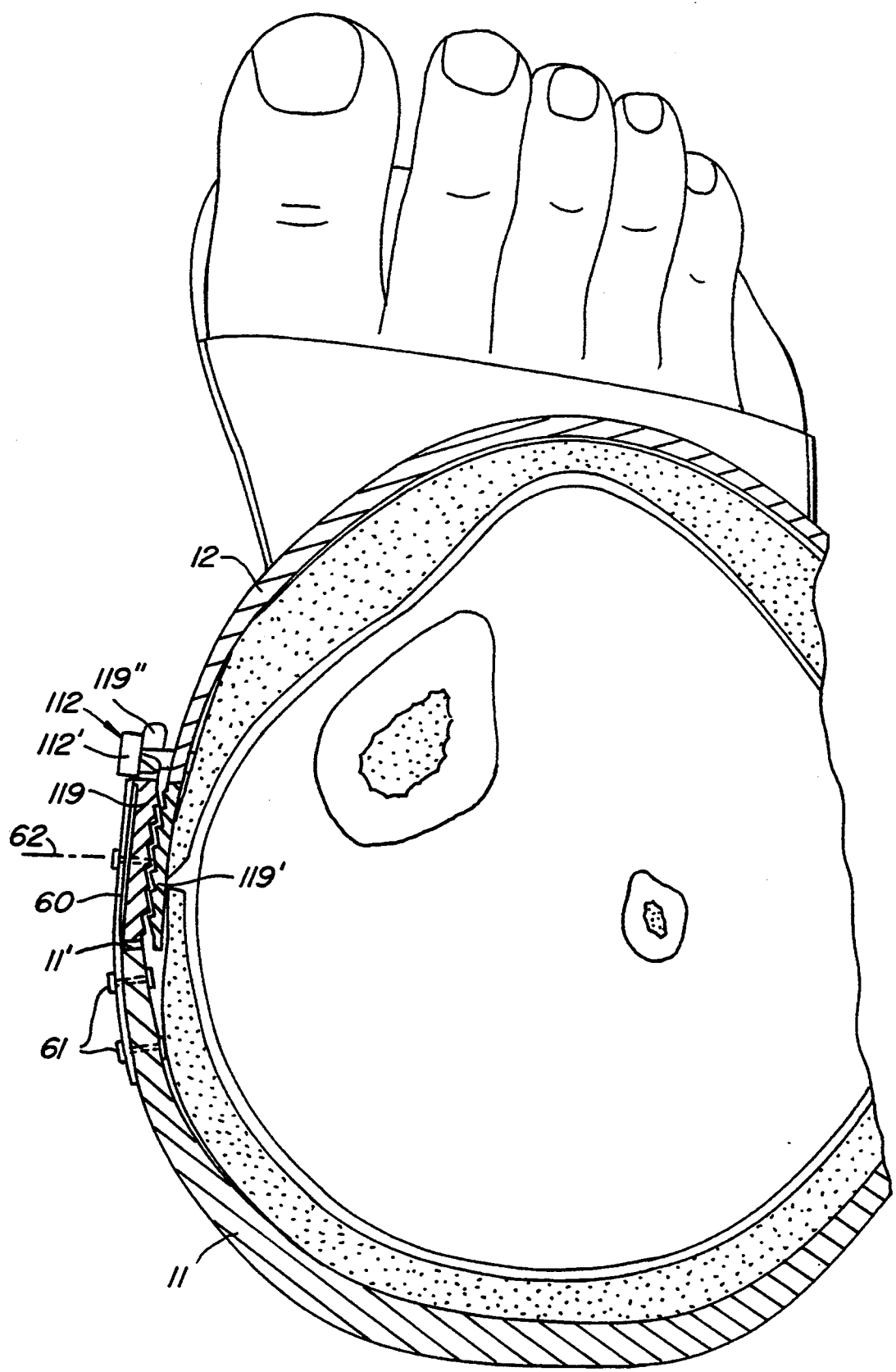

FIG. 6 shows a further embodiment of the apparatus of the invention in which the closure devices consist of latch devices with latch elements 119, 119' which can be plugged into one another and have a plurality of latch positions. In this embodiment the free edges of the shaft part 11 engage over the free edges of the shaft cover shell 12 so that the free edges of the shaft cover shell 12 are disposed between the free edges of the shaft part 11 and the associated cushion.

Openings 11' are provided in the region of the free edges of the shaft part 11 and a latching element 119 resiliently engages through the openings. The latching element 119 has in this arrangement latching teeth at its inner side and is secured at its outer side, preferably so that it is rotatable about a transverse axis 62, to a spring element 60 mounted on the shell part 11 in customary manner, for example by means of rivets 61. The spring 60 is thereby prebiased in such a way that the latch element 119 is biased inwardly through the opening 11'.

Rigid counter-latching elements 119' are provided at the free edge region of the shaft cover shell 12 and the latch teeth of the counter-latching elements 119' are directed outwardly in order to cooperate with the latch teeth of a latch element 119 disposed at the same height. The rotatability of the latch element 119 about the transverse axis 62 thereby ensures that the position of the rotatable latch element 119 adapts to the longitudinal extent of the latch teeth of the rigid element 119'.

In order to provide a counter-abutment necessary for reliable latching mushroom spigots 112 are provided on the shaft cover shell 12 in the vicinity of the counter-latching elements 119', preferably above and below the counter-latching elements 119', and engage at the same level into slots 119" in the shaft part 11, likewise preferably above and below the associated latching element 119, with their mushroom heads 112' engaging outwardly over these slots.

The resiliently outwardly deflectable latching elements 119 can preferably be blocked in the respective latching position and are in particular lockable by means of a separate actuating member so that unauthorised opening of the latching and thus opening of the apparatus is prevented. By way of example a security of this kind of the outwardly deflectable latching element 119 can be formed by a radially projecting rotatable disk provided with noses and mounted on the spring element 60, with the noses engaging in grooves provided in the shaft part 11 in the manner of a bayonet connection. The rotatable disk can in this arrangement be so shaped that it can only be rotated by means of a special tool. If ramp surfaces are moreover provided on the shaft part for the noses then the resilient latching element 119 can also be brought by rotation of the disk into a raised opened position and fixed there. In this position problem-free release of the latching device can then be carried out.

Figure 5:
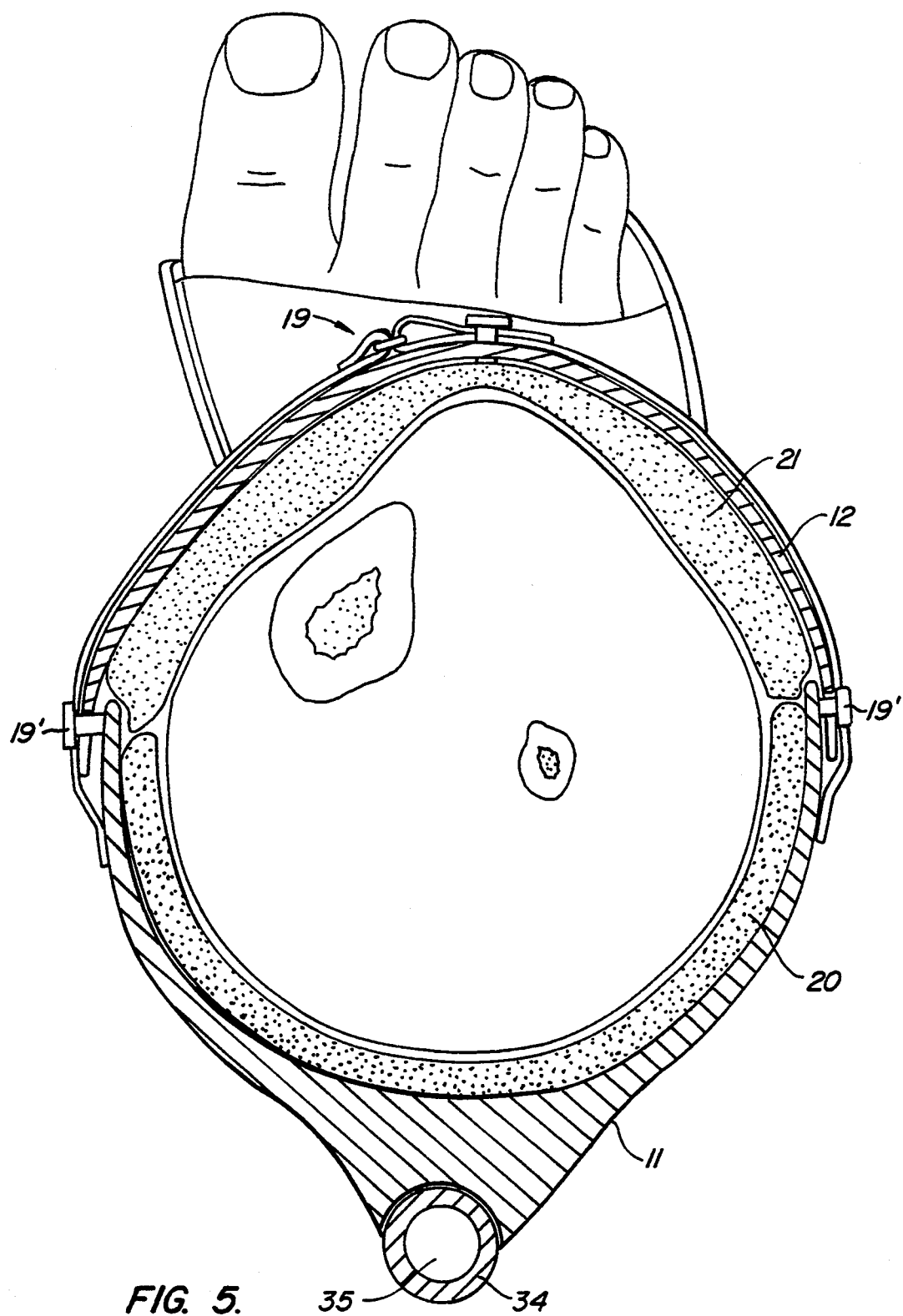

Such latching devices can naturally also be provided at the outer side of the apparatus and also on the foot part 10 and on the foot cover shell 13. Moreover a mixed utilisation of the described latching devices and the clamping devices shown in FIG. 5 is possible.

Figure 7:
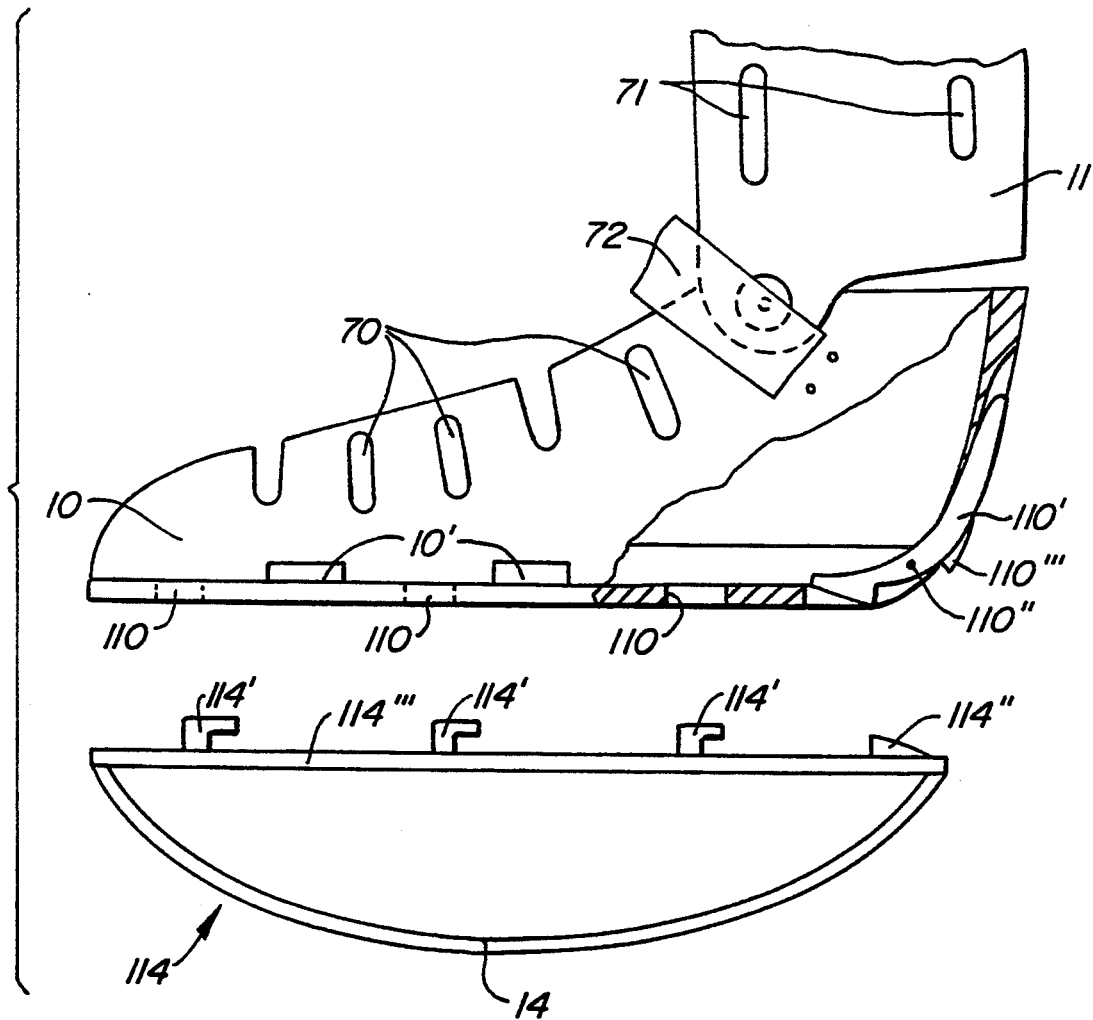

FIG. 7 shows a further embodiment of the apparatus of the invention in which the walking sole is removable. The foot part 10 thereby has openings 110 at its lower side which are preferably formed as elongate holes which extend in the longitudinal direction of the foot part. The removable walking sole part 114 is provided with a downwardly arched walking sole 14 and has at its upper side which faces towards the foot part 10 a rigid mounting plate 114'''. Hooking elements 114', are formed on the mounting plate 114''' —associated with each opening 110 in the foot part—which project upwardly out of the mounting plate and have a rearwardly directed hook-like formation.

At the rear end of the mounting plate 114''' there is formed a counter-latching element 114" provided with a forwardly directed latch edge. A resiliently journalled latching lever 110' associated with this counter-latching element 114" is provided in the heel region of the foot part 10.

For the mounting of the walking sole part 114 on the foot part 10 the walking sole part 114 is pressed from below against the foot part 10 with the hooking elements 114' penetrating into the openings 110. The walking sole part 114 is then pushed rearwardly with the hook-like formations of the hooking elements 114' engaging over the rear edge of each opening 110. At the same time during the rearward displacement of the walking sole part 114 the latching lever 110' is pivoted outwardly from the oblique rear edge of the counter-latching element 114" and its latch surface snaps in the rearmost position of the walking sole part 114 in front of the latch surface of the counter-latch element 114". In this manner the walking sole part 114 is reliably secured to the foot part 10.

For the release of the walking sole part 114 the latching lever 110' is engaged at its rear upwardly standing actuating lever and this is pressed downwardly with the latch lever 110' being pivoted about its pivot axis 110" (in the clockwise sense in FIG. 7) and releasing the counter-latching element 114". An ejector projection 110''' which is likewise provided on the latching lever 110' presses against the rear edge of the mounting plate 114''' of the walking sole part 114 on further pivoting of the lever 110' and pushes the latter forwardly so that the hooking elements 114' can emerge out of the openings 110' of the foot part 10. In this manner a single handed release of the running sole part 114 from the foot part 10 is possible without additional tools.

A removable walking sole part of this kind is advantageous with respect to hygene since it can be removed by the patient when he gets into bed with the apparatus. At the same time, with multiple use of the apparatus the walking sole part which is formed as a part subjected to wear can be simply replaced at favourable cost.

A further advantage of a removable walking sole part of this kind is to be seen in the fact that the apparatus can be used without a walking sole part as a substitute for a "reclining plaster" and the patient is able to recognise that he is not permitted to walk with the apparatus without the walking sole. Only when, for example the doctor in charge of the treatment, hands the walking sole to the patient is this a clear sign to the patient that he can now walk and again load the leg.

In FIG. 7 vent openings 70 and 71 are furthermore formed in the foot part 10 and in the shaft part 11. These vent openings 70, 71 are parts of a vent system which should be described later for the body parts which are received in the apparatus.

Furthermore, outwardly opening drainage channels 10' are provided in the base of the foot part 10 the region of the foot contact surface to drain off liquid which collects in the foot part. The intermediate sole 50 arranged in the foot part and also the foot bed 51 are provided in this case with (non-illustrated) openings which open into the drainage channels 10' and permit the drainage of perspiration which is given off by the foot, or of water which enters into the apparatus.

Figure 8:
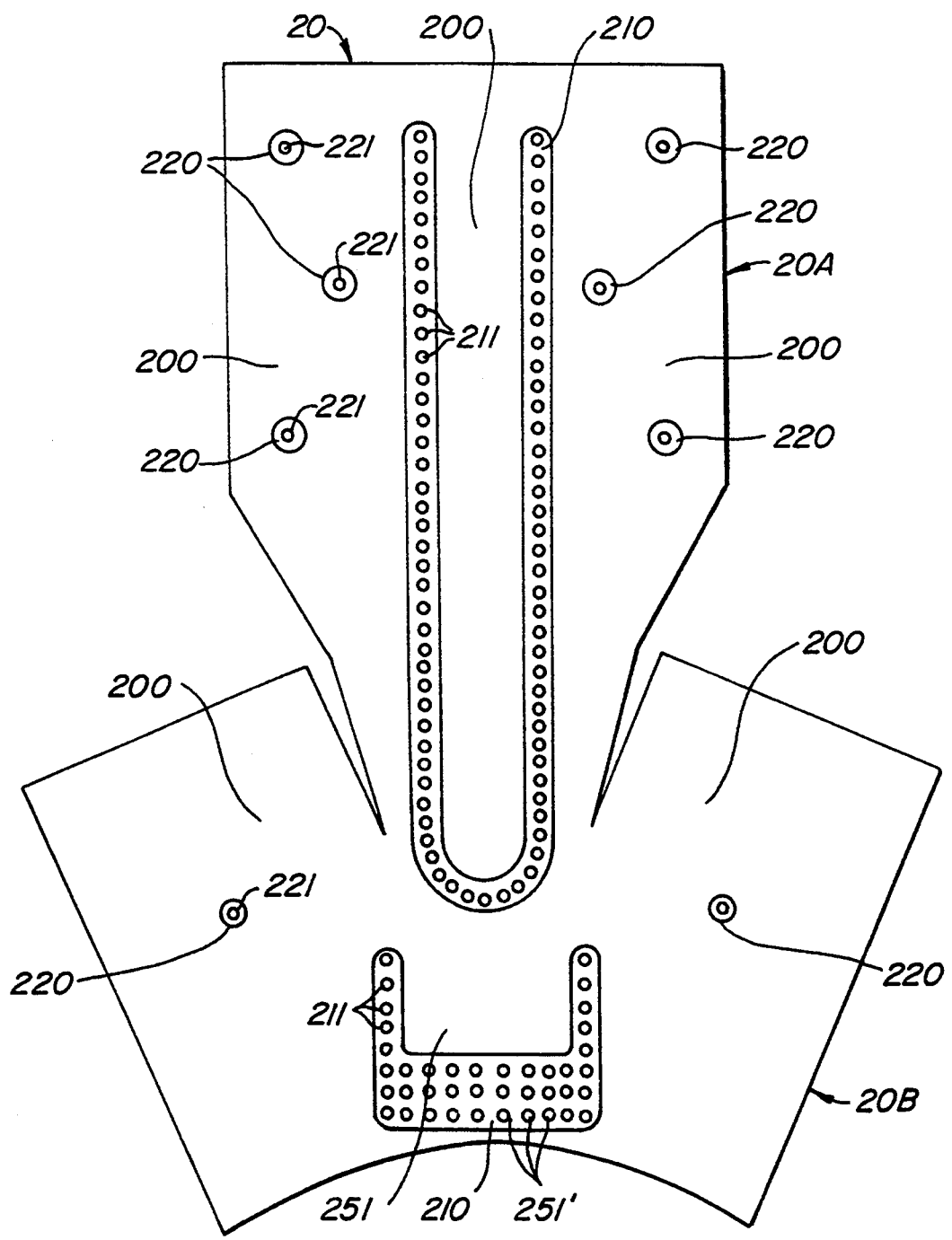

In FIG. 8 there is shown a flat evacuatable cushion with the valve lying on the non-visible rear side. The cushion has a plurality of vacuum-tight regions 200 which are connected together and filled with filling bodies with webs 210 and islands 220 being formed between these regions. The webs 210 and the islands 220 are provided with air passage openings 211, 221. The webs 210 thereby extend preferably in the direction of the longitudinal extent of the cushion 20.

In the evacuated state of the cushions the webs form aeration and venting channels. Further aeration and venting channels are formed by negative folds in the cushion which arise during evacuation of the cushion, so that channels also form between the islands 220 and the webs 210. An air exchange between the surface of the surrounded body part and the outer side of the cushion surrounding this body part can take place through these channels and the air passage openings 211, 221. The uneven surface of the cushion brought about by the filling bodies in the evacuated state also ensures the formation of smallest aeration and venting channels.

The cushion 20 is arranged in the shell parts in such a way that at least the channels formed by the webs 210 and preferably also the islands 220 are disposed in the region of the air passages 70, 71 of the associated shell part 11, 12. In this way the air exchange between the surrounded body parts and the outer side of the apparatus is ensured.

The shaft cover shell 12, the foot cover shell 13 and the associated cushions 21, 22 can be formed in analogous manner.

The cushion 20 is provided at least at the side facing the body part to be surrounded with a dry layer which serves to transport away moisture and an adjoining moisture collecting storage layer. In this way a climatic system is provided which ensures a reliable aeration of the surrounded body parts and which simultaneously ensures the transport of moisture away from the skin of the surrounded body parts. The filling of the cushion with polystyrene thereby simultaneously ensures a thermal insulation of the surrounded body parts which is for example advantageous, particularly in winter.

The cushion 20 shown in FIG. 8 consists of an upper shaft section 20 A and of a lower foot section 20 B. In this manner both the lower leg and also the foot of a patient can be surrounded with a single evacuatable cushion. In the central region of the foot section 20 B a vacuum-tight region is formed as the foot bed 251 with the contour of this region being matched during evacuation of the cushion 20 to the foot arch of the patient and in this way simultaneously supporting the foot. Air passage openings 251' are likewise formed beneath the foot which open into drainage channels 10' and thus serve to lead away liquid out of the region beneath the foot.

Figure 9:
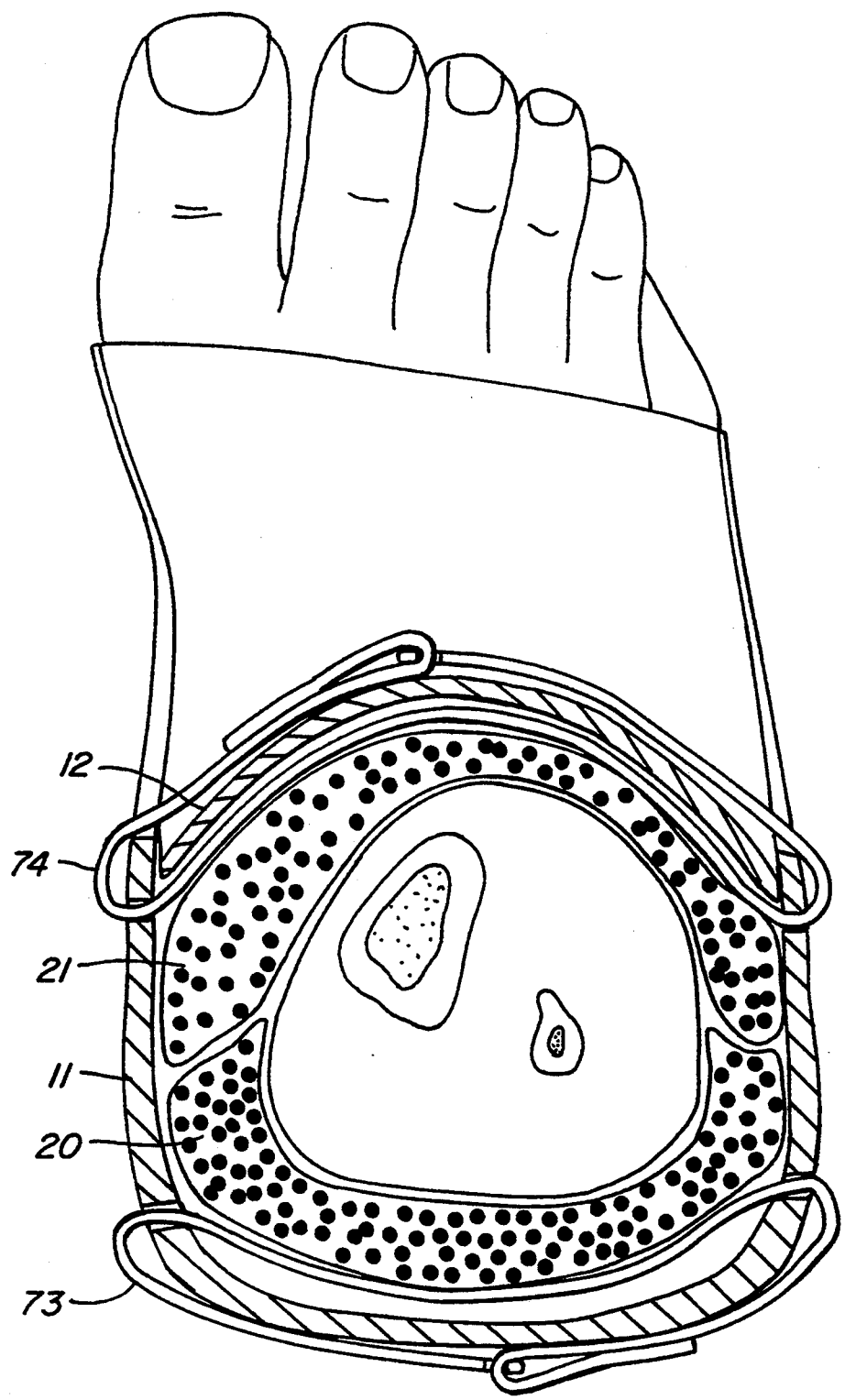

A clamping element, in particular a clamping hook 72 can be hinged to the foot part 10 or to the shaft part 11, in particular adjoining the pivot hinge 15 in the region of the transition from the foot part 10 to the shaft part 11, in order in this region to achieve both a transverse clamping and also the pressing of the associated shaft cover shell onto the foot (FIG. 7). This clamping hoop 72 counteracts the lateral bending up in this region which is brought about by the elasticity of the material of the shell parts and thus, in this region, also presses the shaft part and the foot part sideways against the body part to be surrounded. A further particular embodiment of the apparatus of the invention is shown in FIG. 9 with the shaft region being sectioned at the level of the line IX—IX shown in FIG. 3. A clamping band 73 is provided in the rear region of the shaft part 11 and passes through the shaft part 11 from the left to the right, with the clamping band 73 being guided through lateral openings of the shaft part 11. At the rear outer side of the shaft part 11 the clamping band 73 is guided in customary manner through a loop. At the inner side of the shaft part the clamping band is disposed between the shaft part 11 and the cusion 20.

If now the clamping band 73 is tensioned then the region of the clamping band 73 disposed inside of the shaft part 11 is stretched whereby a pressure which is forwardly directed in the foot direction as exerted on the cushion 20. This pressure brings about a forward displacement of the foot and in particular of the ankle joint and thus brings about a fixation of the enclosed body part in this front position.

Alternatively to this a clamping band 74 can be provided in the front region of the shaft part 11, with the clamping band 74 passing through lateral openings in the region of the free edge of the shaft part 11 with its inner section coming to lie between the front cushion 21 and the shaft cover shell 12. The outer sections of the clamping band 74 are guided outwardly around-the shaft cover shell 12 and are there clamped to one another.

A firm tensioning of the forwardly arranged clamping band 74 thereby brings about a pressure from the front onto the front cushion 21 and thus presses the foot, and in particular the ankle joint rearwardly towards the shaft part 11 or towards the heel region of the foot part 10 and fixes it this position.

In specific later healing phases the evacuation of the cushions 20, 21, 22 can be replaced by the application of a light excess pressure whereby a desired massage effect results which is assisted by the particles contained in the cushion.

We claim:

1. An apparatus for treating a fracture in an extremity comprising:
    first and second rigid shell parts coupled together for surrounding the extremity;
    at least one cushion positioned between the shell parts and the extremity, the cushion having an interior wall and an exterior wall defining a vacuum tight inner space therebetween, the cushion having at least one evacuation valve for evacuating the inner space, only a portion of the cushion being connected to the rigid shell parts;
    a plurality of filling bodies movable relative to one another disposed in the inner space of the cushion; and
    means for adjusting an internal diameter of the rigid shell parts to adapt the rigid shell parts to varying sizes of the cushion after the cushion has been applied about the extremity and evacuated.

2. The apparatus of claim 1 wherein the adjusting means comprising a plurality of closure members, the second shell part forming a bottom shell and a first cover shell, the bottom and first cover shells connectable to each other by the closure members so to fit around a foot, the first shell part forming a shaft part and a second cover shell, the shaft part and the second cover shell connectable to each other by the closure members so to fit around a lower leg, the shaft part and the first cover shell overlapping each other.

3. Apparatus in accordance with claim 2 wherein the closure members are latch devices with latch elements that engage one another and have a plurality of latch positions.

4. Apparatus in accordance with claim 3, wherein the latch devices include resiliently outwardly deflectable latch elements on the bottom shell and the shaft part and rigid counter-latch elements on the cover shells, the resiliently outwardly deflectable latch elements being lockable by means of a separative actuating member in the respective latched position.

5. Apparatus in accordance with claim 1, further including form-fitted guides connected to one another between the shell parts.

6. Apparatus in accordance with claim 2, further including a walking sole part removably coupled in a form-fitting and force-transmitting manner with a lower side of the bottom shell.

7. Apparatus in accordance with claim 6, wherein the walking sole part has rigid hooking elements that engage openings in the lower side of the bottom shell and a counter-latching element which cooperates with a latch lever resiliently journalled in the bottom shell.

8. Apparatus in accordance with claim 7, wherein the latch lever includes an ejector projection for removal of the walking sole part.

9. Apparatus in accordance with claim 1, further including webs formed between vacuum-tight regions of the cushions, the webs being provided with air passage openings to form venting channels between the vacuum-tight regions.

10. Apparatus in accordance with claim 9, wherein the webs extend essentially along the longitudinal axis of the cushions.

11. Apparatus in accordance with claim 10, wherein the shell parts include a plurality of openings each having a given size and dimension, the openings being positioned in the region of the venting channels formed by the webs.

12. Apparatus in accordance with claim 2, further including drainage channels provided in the base of the bottom shell to direct away liquid which collects in the bottom shell.

13. Apparatus in accordance with claim 1, wherein the cushions include a dry layer opposing the patient to transport away moisture and an adjoining moisture collecting storage layer to collect said moisture.

14. Apparatus in accordance with claim 12, further including a foot bed on an upper surface of the bottom shell formed as a region of an evacuatable cushion containing filling bodies arranged beneath the foot.

15. Apparatus in accordance with claim 14, further including air passage openings provided in the evacuatable cushion arranged beneath the foot, the air passage openings being coupled to the drainage channels so that liquid which collects under the foot flows through the air passage openings.

16. Apparatus in accordance with claim 1 wherein the first and second shell parts are pivotally connected together via lateral hinges, the apparatus further including an adjusting device coupled between the first and second shell parts for adjusting the angle of inclination of the first shell part relative to the second shell part around a hinge axis.

17. Apparatus in accordance with claim 16 wherein the adjusting device has first adjusting nut rotatably coupled to the first shell part, first threaded tube axially displaceable within the first shell part and an anchor pivotally coupled to the second shell part which is hingedly journalled on the foot part, which is screwed into an adjusting nut (32) rotatably journalled on the shaft part (11), which extends and extending through the threaded tube, the anchor having an abutment head at a free end, the abutment head cooperating with an abutment formed by an associated end of the threaded tube.

18. Apparatus in accordance with claim 17 further including a second adjusting nut rotatably journalled on the first shell part above the first adjusting nut and a threaded bar screwed into the second adjusting nut and axially displaceably guided in the in the first shell part, the threaded bar having a lower end facing the abutment head forming a second abutment for the abutment head of the anchor so that a respective individually adjustable abutment is provided above and beneath the abutment head.

19. Apparatus in accordance with claim 18, further including first and second lockable devices coupled to the first and second adjusting nuts to prevent accidental rotation of said nuts.

20. Apparatus in accordance with claim 16, further including vertically adjustable hinges to adjust a lateral inclination of the first shell part relative to the second shell part around an axis perpendicular to the hinge axis.

21. Apparatus in accordance with claim 1, further including inwardly directed projections disposed within the first and second shell parts for the positional fixation of the cushions.

22. Apparatus in accordance with claim 1, further including a clamping device provided on one of the first and second shell parts to press the bottom shell in a horizontal direction.

23. Apparatus in accordance with claim 2, further including a clamping hoop hinged between the bottom shell and the shaft part to press the shaft part into the second cover shell.

* * * * *